United States Patent [19]
Anon

[11] 4,299,215
[45] Nov. 10, 1981

[54] ANTI-CONTAMINATION DEVICE FOR USE IN OPERATING THEATRES

[76] Inventor: Ramon L. Anon, Calle de la Solana, num. 11, Torrejon de Ardoz (Madrid), Spain

[21] Appl. No.: 89,910

[22] Filed: Oct. 31, 1979

[30] Foreign Application Priority Data

Jan. 19, 1979 [ES] Spain ............................... 240.864[U]

[51] Int. Cl.³ ........................................... A61M 16/00
[52] U.S. Cl. ............................. 128/200.24; 128/910; 128/205.17; 128/205.19
[58] Field of Search ................... 128/910, 200.24, 139, 128/201.29, 202.19, 205.19, 205.12, 205.27, 205.29; 55/319, 279, DIG. 33, DIG. 35

[56] References Cited

U.S. PATENT DOCUMENTS 4,071,338  1/1978  Hutter et al. .................. 128/910 X

FOREIGN PATENT DOCUMENTS 670977  1/1939  Fed. Rep. of Germany ...... 128/910
786243  6/1935  France .............................. 128/910
306854  7/1971  U.S.S.R. ......................... 128/205.29

Primary Examiner—Henry J. Recla
Attorney, Agent, or Firm—Bucknam and Archer

[57] ABSTRACT

An apparatus for filtering respiratory gases expired by a patient to prevent contamination of the surrounding atmosphere. Gases from the patient enter a bag and are drawn through a membrane filter by the action of a vacuum collection system.

9 Claims, 1 Drawing Figure

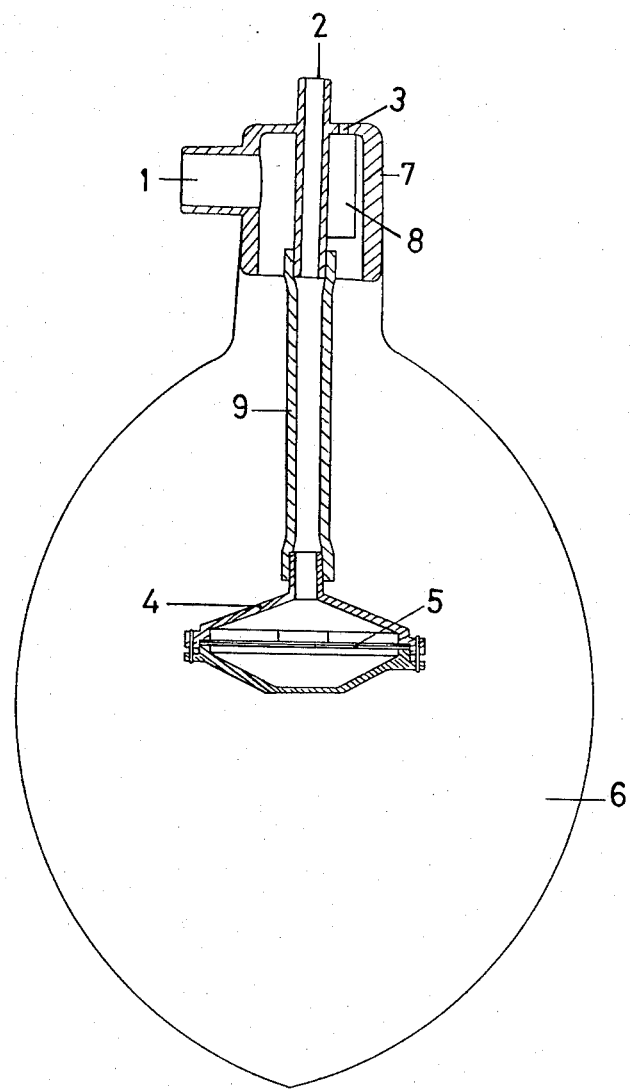

ANTI-CONTAMINATION DEVICE FOR USE IN OPERATING THEATRES

This invention relates in general to apparatus for filtering respiratory gases, and more particularly to an anti-contamination device for use in operating theatres to prevent contamination of the atmosphere by respiratory gases expired by a patient.

As we already know, during the normal activity of operating theatres, the gases expired by the patient mix with the atmospheric air and contaminate from both the bacteriological and chemical points of view.

The first of these forms of contamination is clear and although it is not important in most cases, it may be so in the case of patients with some kind of infection and particularly if this is highly contagious. The possible direct recipients of the said contamination are naturally the medical, maintenance and cleaning staff in the hospital and by extension, the new patients subsequently operated on in the same operating theatre.

The chemical form of contamination is due to the constant introduction of nitrous oxide, anesthetic agents and to the air in the operating theatre as if the latter is fitted with an adequate ventilation system, it will never contain concentrations high enough to produce effects of anesthesia on the people working there. However, there is evidence in medical bibliography that this kind of contaminating agents have harmful effects on the health of the doctors and hospital staff constantly exposed to them.

From this brief explanation of constant risks, one may clearly deduce the need for eliminating or reducing as much as possible, the contamination of operating theatres produced by the patients' respiratory gases, which constitutes the main objective which is fully achieved with the device which we shall now describe.

The anti-contamination device for use in operating theatres which we propose has as its main function the collection of the gases aspired by the patient and it transfers them outside the operating theatre by means of a centralized vacuum duct and in order to prevent biological contamination, this device is fitted with an absolute membrane filter able to retain the microorganisms carried in the aspiratory gases.

The design of the said device envisages, firstly, a body which serves as a general support to the components and is connected to both the patient's circuit and that of the vacuum system.

An elastic bag is fitted around the lower part of the said body and inside, in the centre of the same, a connecting tube with the filter-holder fastened to the same at the free end, thereby securing it to the general support body.

Inside the said filter-holder there is an absolute membrane filter in which the anti-contaminating function takes place.

The general support body and the filter-holder are best made from an injectable, plastic material, compatible with the demand for ideal functioning, with the elastic bag preferably made from latex.

In the detailed description which follows, we refer to the single diagram enclosed which, as an example and with no limiting nature whatsoever, as practice may make minor modifications advisable without altering the essential nature of the invention, represents the implementation which we consider to be ideal for the function envisaged, the specifications of which cover each of the parts of the device described.

The gases intermittently expired by the patient are passed inside the elastic bag 6 via the intake 1 of the general support body 7 with the said bag acting, within the normal limits of respiratory volumes and frequencies, as a highly ductile container.

The vacuum system, connected to the device by the intake 2 aspires the gases contained in the elastic bag 6 trasfering them through the absolute filter 5, supported by the filter-holder 4 and through the connecting tube 9. In the said aspiration of the vacuum system, the said filter retains all the particles and germs carried by the gases.

In order to ensure that the device does not affect the functioning of the anesthesia equipment upon which it is mounted, it is necessary to guarantee that the aspired gas intake 1 allows at all times for a pressure equal to the atmospheric pressure, this balance being achieved by the complementary action of the elastic bag and the orifice 3 which enables air to enter when the average amount expired by the patient is less than that aspired by the vacuum duct through the absolute membrane filter and it prevents the pressure of the latter from building up inside the bag.

A series of partitions 8 placed inside the general support body 7 effectively prevent the gases expired by the patient from escaping directly into the atmosphere and it may be deduced from this that these elements are of vital functional importance in the device which we propose.

In the technical specifications, it must be pointed out by means of a correct gauging of all of the parts which go to make up the device, it is possible to specify the following characteristics:

Efficiency 95% (the percentage of gases expired by the patient and transferred to the vacuum duct).

Maximum capacity 16 lt/min.

Respiratory frequency: 10-50 resp/min.

Pressure in the gas intake: Atmospheric ±1 cm. H20.

Minimum vacuum: 350 mm Hg.

Running time: 8 hours (This period will be considerably affected by the patient's ventilation. The greater the latter, the greater the running time of the device.)

From the foregoing the artisan will appreciate that the invention provides an apparatus for filtering respiratory gases, and this apparatus basically comprises a chamber, expediently in the form of an elastic bag 6, having an inlet 1 disposed to receive respiratory gases to be filtered; a conduit including the connecting tube 9 and the tube in the support body 7 having the outlet 2, which conduit extends into the chamber defined the bag 6 to accommodate the outflow of filtered respiratory gases therefrom. The conduit has an inlet within the chamber, which inlet can be associated with the connecting tube 9 and portion of the filter holder 4 directly connected to the end of tube 9. A filter 5 disposed within the chamber is interposed across the inlet of the conduit to filter respiratory gases in the chamber as such gases pass through the filter 5 into the tube 9 of the conduit for outflow therethrough and exit at the outlet 2 which is connected to a vacuum source (not shown).

Other variations and advantages of the invention will become apparent to the artisan from the foregoing description of the invention in connection with the drawing.

What is claimed is:

1. An apparatus for filtering respiratory gases, which comprises a chamber having a boundary wall defined by an elastic bag and inlet means disposed to conduct respiratory gases into said elastic bag to be filtered; conduit means disposed for communication with a vacuum source outside said chamber and adapted to extend into said chamber to accomodate the outflow of filtered respiratory gases therefrom under the action of such vacuum source, said conduit means having an inlet within the chamber; and a filter disposed within the chamber and interposed across the inlet of said conduit means to filter respiratory gases in the chamber as such gases pass through the filter into the conduit means for outflow therethrough.

2. An apparatus according to claim 1 wherein said filter is supported by a filter holder connected to said conduit means for support thereby.

3. An apparatus according to claim 1 wherein said filter is a membrane filter effective to block the passage therethrough of microorganisms.

4. An apparatus according to claim 1 wherein said elastic bag is made of latex.

5. An apparatus according to claim 1 including a support member connected to said conduit means and to said chamber to support same.

6. An apparatus according to claim 5 wherein said support member and conduit means are made of plastic.

7. An apparatus according to claim 5 wherein said conduit means extends through said support member and has an outlet on the outside of said support member disposed for connection to a vacuum source.

8. An apparatus according to claim 5 wherein said chamber is defined by an elastic bag and said support member has an orifice disposed to admit into said chamber atmosphere air to establish a given pressure balance between the inside of the chamber and the outside atmosphere.

9. An apparatus according to claim 8 including partition means disposed in said support member and positioned in relation to said orifice to prevent escape into the outside atmosphere of unfiltered respiratory gases in said chamber.

* * * * *